United States Patent [19]

Nunan

[11] Patent Number: 4,868,844
[45] Date of Patent: Sep. 19, 1989

[54] MUTILEAF COLLIMATOR FOR RADIOTHERAPY MACHINES

[75] Inventor: Craig S. Nunan, Los Altos Hills, Calif.

[73] Assignee: Varian Associates, Inc., Palo Alto, Calif.

[21] Appl. No.: 168,621

[22] Filed: Mar. 7, 1988

Related U.S. Application Data

[63] Continuation of Ser. No. 905,988, Sep. 10, 1986, abandoned.

[51] Int. Cl.[4] .............................................. G21K 1/04
[52] U.S. Cl. .................................. 378/152; 378/147; 378/204; 378/150
[58] Field of Search ........................ 378/147, 148–153, 378/154, 155, 157, 158, 145, 204, 205, 160

[56] References Cited

U.S. PATENT DOCUMENTS

| | | | |
|---|---|---|---|
| 2,844,736 | 5/1954 | Johns et al. | 378/152 |
| 2,881,329 | 1/1956 | Peyser | 378/152 |
| 2,959,680 | 11/1960 | Green | 378/152 |
| 3,755,672 | 8/1973 | Edholm et al. | |
| 3,942,019 | 3/1976 | Claridge | |
| 4,233,519 | 11/1980 | Coad | |
| 4,246,488 | 1/1981 | Hura | 378/151 |
| 4,359,642 | 11/1982 | Heinz | |
| 4,365,341 | 12/1982 | Lam | |
| 4,463,266 | 7/1984 | Brahme | |
| 4,464,778 | 8/1984 | Goldmann | 378/151 |
| 4,672,212 | 6/1987 | Brahme | 378/150 |
| 4,672,652 | 6/1987 | Huttenrauch et al. | |
| 4,726,046 | 2/1988 | Nunan | |
| 4,739,173 | 4/1988 | Blosser et al. | 378/152 |
| 4,754,147 | 6/1988 | Maughan et al. | |
| 4,794,629 | 12/1988 | Pastyr | |

FOREIGN PATENT DOCUMENTS

| | | |
|---|---|---|
| 0193509 | 9/1986 | European Pat. Off. |
| 2753397 | 6/1978 | Fed. Rep. of Germany |
| 2759073 | 7/1979 | Fed. Rep. of Germany |
| 3335802 A1 | 4/1985 | Fed. Rep. of Germany |

OTHER PUBLICATIONS

H. Perry, J. Mantel, J. J. Weinkam, and M. M. Lefkofsky, "Computer Control of Patient and Machine Parameters in Radiation Therapy", *Proceedings Seventh International Conference On the Use of Computers in Radiation Therapy*, The Japan Radiological Society, 1981, pp. 21–27, Sep. 22–26, 1980.

Matsuda and Inamura, "Computer Controlled Multi-Leaf Conformation Radiotherapy", *Nippon Acta Radiologica*, Oct. 25, 1981.

Matsuoka and Inamura, "Computer Controlled Multi-Leaf Conformation Radiotherapy", Tokyo Metropolitan Komagome Hospital.

Chin et al., "A Computer-Controlled Radiation Therapy Machine for Pelvic and Para–Aortic Nodal Areas", *Int. J. Radiation Oncology, Biol. Phys.*, 7, pp. 61–70, 1981.

Davy et al., "Conformation Therapy Using the Tracking Cobalt Unit", *Brit. J. Radiology*, 48, pp. 122–130, 1975.

Ueda, "Application of Conformation Radiotherapy and its Technical Problems", *Proc. Japanese Radiation Technology Society*, 32nd meeting, pp. 1–46, Sep. 1976.

Bess, L.; Ovadia, J.; Valassis, J.; "External Beam Current Monitor for Linear Accelerators", *Rev. Sci. Instr.*, vol. 30, pp. 985–988, 1959.

Menke, J. L., "Beam Monitoring at the NBS Linac-Energy, Positioning, Current, Charge", *I.E.E.E. Trans on Nuclear Science*, No. 3, pp. 921–922.

Mohan et al., "Use of Fast Fourier Transforms in Calculating Dose Distributions for Irregularly Shaped Fields for Three-Dimensional Treatment Planning", *Med. Phys.*, 14, pp. 70–77, 1987.

Primary Examiner—Carolyn E. Fields
Assistant Examiner—Joseph A. Hynds
Attorney, Agent, or Firm—Stanley Z. Cole; Gerald M. Fisher; Kenneth L. Warsh

[57] ABSTRACT

In a radiation therapy machine it is desirable to produce irregular radiation field shapes in order to shield critical organs not invaded by the tumor. A multileaf collimator is formed of a multiplicity of heavy metal bar leaves driven relative to frames which are driven relative to jaws of a rectangular field collimator by electric motors and flexible cables.

10 Claims, 4 Drawing Sheets

FIG.2
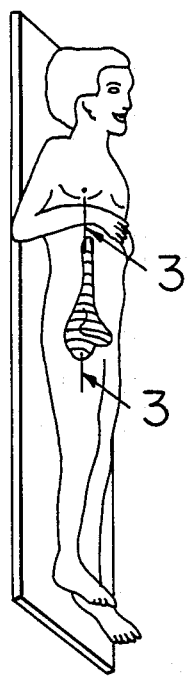
FIG.3
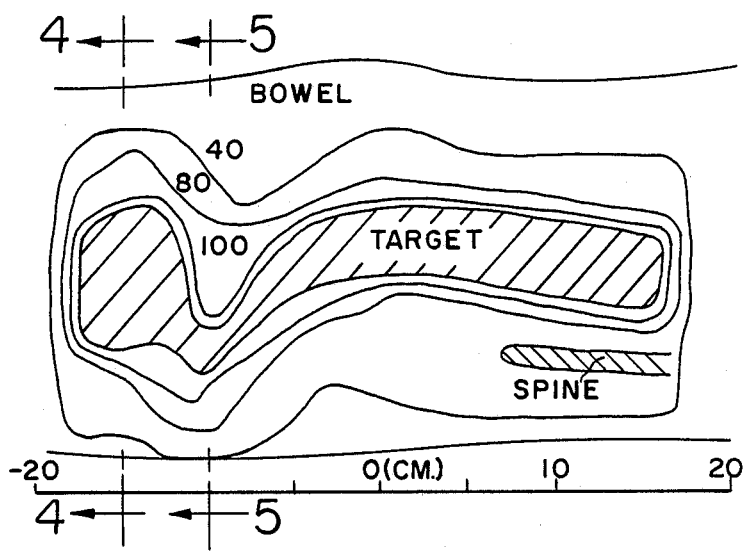
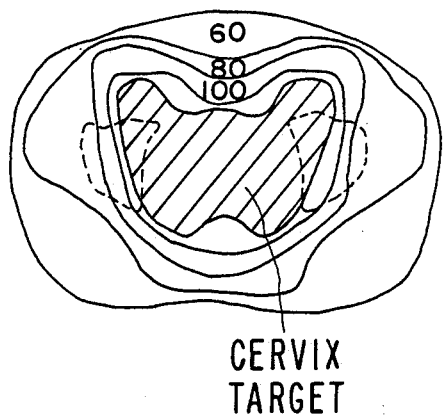
CERVIX
TARGET
FIG.4
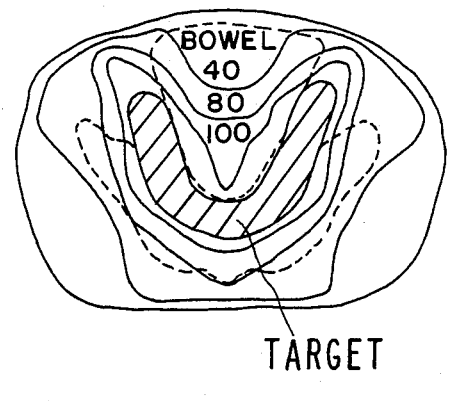
TARGET
FIG.5

MUTILEAF COLLIMATOR FOR RADIOTHERAPY MACHINES

This application is a continuation of application Ser. No. 905,988, filed 9/10/86 now abandoned.

FIELD OF THE INVENTION

This invention pertains to an apparatus for shaping the radiation field in a radiotherapy machine.

BACKGROUND OF THE INVENTION

In conventional x-ray therapy, rectangular field shapes are formed by four motor driven jaws in the radiation head. Irregular field shapes for individual portals are then produced by mounting shadow blocks on a shadow tray between the jaws and the patient. The shadow blocks shield critical organs not invaded by the tumor. The radiation beam can be directed at the prescribed treatment volume from a single direction (single port therapy), from two or more directions (multi-port therapy), or the beam can be swept through an arc (arc or rotation therapy), all by rotating an isocentric gantry, for example. A cylindrical-shaped region of high dose is produced by a rectangular field in multi-port, arc or rotation therapy.

In multi-port therapy, the shadow blocks are changed for each beam angle. This can require that the technologist go back into the shielded treatment room for each treatment field, a time-consuming process. If the beam angle is not vertical, the shadow blocks must be locked to the shadow tray (to avoid their falling off), which can be awkward and time-consuming. The shadow blocks are typically made by pouring a heavy metal into a pre-cut mold, which is also time-consuming. The shadow blocks can be heavy, difficult to handle, and dangerous if they fall on the patient or the radiotherapy personnel.

In arc or rotation therapy, it is not practicable to change the shadow blocks continually or in small steps of beam angle.

The usual treatment field shapes result in a three-dimensional treatment volume which includes considerable volume of normal tissue, thereby limiting the dose that can be given to the tumor volume. The irradiation dose that can be delivered to a portion of an organ of normal tissue without serious damage can be increased if the size of that portion of the organ receiving such radiation dose can be reduced. Avoidance of serious damage to the organs surrounding and overlying the tumor determines the maximum dose that can be delivered to the tumor. Cure rates for many tumors are a steep function of the dose delivered to the tumor. Techniques are under development to make the treatment volume conform more closely to the shape of the tumor volume, thereby minimizing the product of volume and dose to normal tissue, with its attendant effects on the health of the patient. This can permit higher dose to tumors or can result in less damage to normal tissue. These techniques involve moving the x-ray jaws during treatment or scanning the x-ray beam or using multi-leaf jaws.

In a technique called dynamic therapy, one set of jaws is set to form a narrow (e.g., 4 cm) fan beam and the spread of the fan beam is varied by the second set of jaws to conform to the boundaries of the prescribed treatment volume as the beam angle is swept or stepped around the patient and as the patient and associated table top are moved through the fan beam. A computer controls the movements of the table top in x, y and z, the gantry angle, the upper jaws during start and stop of the scan, the lower jaws throughout the scan, and the dose rate. The complexity is such that great care must be exercised in preparing for such treatments, which consumes considerable time.

A technique has been proposed in which a narrow collimated lobe of x-rays is scanned over the treatment field, permitting production of irregular field shapes at selected beam angles. Because only a small fraction of the x-ray output is within the narrow lobe, the effective dose rate is low and the time to produce a portal field is hence long and multi-port treatment times are excessively long. Also, scanning individual fields is not readily applicable to arc and rotation therapy modes.

Machines have been built in which each of the lower pair of jaws is divided into a number (e.g., 5 to 32) of narrow bars called leaves. Each leaf may be about 10 cm thick (in the beam direction) to provide adequate attenuation of the x-ray beam (down to about 1%), about 0.5 to 1.5 cm wide and about 14 cm long. Each leaf can be moved independently by a motor drive. This permits the production of irregularly shaped fields with stepped boundaries, thereby avoiding shadow blocks for many situations in portal therapy. The shape can be changed as the beam direction is swept in arc or rotation therapy. The disadvantage of this technique of replacing the lower jaws by a multiplicity of leaves is that each leaf is quite large and heavy, requiring a motor drive system which consumes considerable space. There is limited room in the radiation head for all these components so either sacrifices in performance are made (such a fewer leaves, limited field size) or the construction costs become large.

In a different technique, the conventional upper and lower pairs of jaws are retained and a set of leaves is mounted between the jaws and the patient. Each leaf moves in a plane, driven by a rotating cam or pushed by a form corresponding to the desired irregular field shape. In one early concept, each leaf was thick enough to attenuate the x-ray beam to the required level (to about 5% of unattenuated beam intensity), the ends and sides of the leaf forming a rectangular parallelpiped, hence not aimed toward the x-ray source. In a recent concept, a multiplicity of small diameter rods forms a stack sufficiently thick to provide the required beam attenuation. Each rod can slide with respect to its neighbors. A form corresponding to the desired field shape boundary is used to push the assembly of rods so that their ends form a similar beam boundary. Since the rods are small in diameter, the radiation field boundary can be relatively smooth (very small steps) and tapered (focused) toward the source. However, varying the field shape as a function of beam angle without entering the treatment room can require a quite complex drive system because the large number of rods requires that they be driven enmasse instead of individually.

OBJECTS OF THE INVENTION

An object of the invention is to provide an accessory to conventional radiotherapy machines which is so compact and lightweight that it can be mounted in the space normally occupied by the conventional wedge mount on the radiation head, retaining the existing radiation shielding jaws and leaving room for a conventional accessory mount for shadow blocks and compensating filter. The accessory is a multi-leaf collimator which provides irregular field shapes under computer control in order to optimize the radiation dose distribution delivered in a treatment volume of prescribed shape, with minimal radiation dose to critical tissues outside this treatment volume.

A further object is to expedite patient flow in a radiotherapy department by eliminating much of the time that radiation therapy personnel now spend in preparing radiation shadow blocks and in positioning these blocks on the radiotherapy machine with respect to the patient for each treatment field.

SUMMARY OF THE INVENTION

These objects of the invention and other objects, features and advantages to become apparent as the specification progresses are accomplished by the invention according to which, briefly stated, a compact lightweight accessory to radiotherapy machines is comprised of a multiplicity of straight heavy metal bars of rectangular cross-section, called a multi-leaf collimator. The collimator included two multi-leaf half-assemblies, left and right. Each multi-leaf half-assembly is mounted on a frame half-assembly. Each of the two frames half-assemblies can be moved in synchronism with the corresponding radiation shielding jaws of the conventional head of a radiotherapy machine, or can be moved independently of these jaws. This permits conventional therapy to full field size using the jaws with leaves retracted, and permits formation of irregular fields by extending appropriate leaves into the rectangular field defined by the jaws. These irregular field shapes can be varied during rotation of the radiotherapy machine gantry by driving the individual leaves with respect to their frame and driving the frame with or respect to the corresponding jaw. It permits production of wedged dose distributions by moving the leaves across the field during a portal treatment. The leaves are short because they need to be only as long as the maximum extension into the rectangular field defined by the jaws. Because the leaves are small, hence light weight, the drive system is small and light weight. The entire assembly of two half-assemblies, each with its multiplicity of leaves and motor drives is contained within a flat cylinder corresponding in size approximately to the wedge mount used in conventional radiotherapy machines, being about 2 inches thick and 2 feet in diameter. This maintains necessary clearance around the patient and patient table and maintains convenient access to the patient by radiotherapy personnel. Each frame half-assembly comprises a frame and a sub-frame, one above the other. The sub-frame which is further from the radiation source is motor-driven slightly faster than the sub-frame which is closer to the source. Each leaf comprises two sub-leaves, one above the other. The sub-leaf further from the radiation source is slightly wider than the sub-leaf closer to the source and is motor driven slightly faster. The approximate focusing on the x-ray target obtained by the difference in speed of drive of the frame and sub-frame and the two sub-leaves thereby avoids excessive beam penumbra. The sides of the sub-leaves form steps which close off direct irradiation from the source through the gaps between adjacent leaves, yet produce small radiation penumbra since their lips are in a plane containing the source. The ends of the sub-leaves extending into the radiation field also form steps which produce small penumbra since their lips remain in a plane containing the source over the full range of leaf travel. To produce wedge-shaped dose distributions, a wedge filter can be inserted in the assembly with the leaves withdrawn, the field being defined by the jaws. The leaves are driven through cables (tachometer type) from gear motors which rotate through a given angle (step) in response to a pulse from a microprocessor. Alternatively, hydraulic drive can be used. The resulting position of each leaf is displayed on a CRT. The desired field shape can be input to this CRT via various alternative conventional devices and the leaves driven automatically to reach this shape. The invention has the following advantages:

1. The multi-leaf assembly is planar and fits in the space presently occupied by the wedge mount in conventional wedged portal fields. Alternatively, for portal fields (fixed beam angle), the leaves can be driven as a mono-block across a field formed by symmetrically displaced jaws, producing a dynamically wedged field, or the leaves can be retracted and one of the jaws can be driven independently across the field to produce the dynamically wedged field. The cylinder height is so small that the conventional mount for shadow blocks and compensating filters can be retained. Shadow blocks would still be needed to block islands in the radiation field.
2. The conventional jaws of the radio therapy machine are retained and the leaves can be retracted out of the jaw field. Thus, conventional radiotherapy up to full rectangular field sizes is retained. This is an important performance aspect. It is also an important reliability aspect, since a patient's course of radiotherapy can be completed by conventional means in case of failure of the multi-leaf collimator system.
3. The multi-leaf system is an accessory which can be attached to existing machines in place of the wedge mount, rather than requiring major modification of the radiation head to replace existing jaws.
4. Approximate focusing on the x-ray target is provided at both the ends and the sides of the leaves while shielding the gaps between the leaves, and with the leaves being straight bars of rectangular cross-section.
5. Making the bars straight and of rectangular cross-section facilitates economical manufacture and moving them in planes minimizes total assembly height and complexity of drive.
6. The leaves function as extension into the rectangular field defined by the conventional jaws, in essence serving the function of dynamic shadow blocks. Their movement can be in concert with or independent of the movement of the jaws. This arrangement minimizes the size and weight of the leaves and hence of the drive system for the individual leaves.
7. The leaves (and sub-leaves) are supported so they do not touch each other, avoiding friction between the leaves in the x-ray field.
8. The compact multi-leaf system can be installed as an accessory on machines producing other types of radiation than x-rays, such as gammas from radioactive sources, neutrons from proton and deuteron accelerators, and proton and electron beams.

These and further constructional and operational characteristics of the invention will be more evident from the detailed description given hereinafter with reference to the figures of the accompanying drawings which illustrate one preferred embodiment and alternatives by way of non-limiting examples.

BRIEF DESCRIPTION OF THE DRAWINGS

FIG. 1 is a view from the x-ray source of multple-leaf fields according to the invention.

FIG. 2 is an illustration of a complex target region for use of the invention, the region of cervix-pelvic nodes-para-aortic lymph nodes region based on: Chin, L. M., et al, "Int. J. Radiation Oncology, Biol., Phys" Vol. 7, pp 61–70.

FIG. 3 is a section of the target region in the patient mid-saggital section plane 3—3 of FIG. 2.

FIG. 4 is a section of the target region in the section plane 4—4 of FIG. 3.

FIG. 5 is a section of the target region in the section plane 5—5 of FIG. 3.

FIG. 9 is a schematic diagram of the connection of the motors to the control computer.

Glossary

Figure 1A:
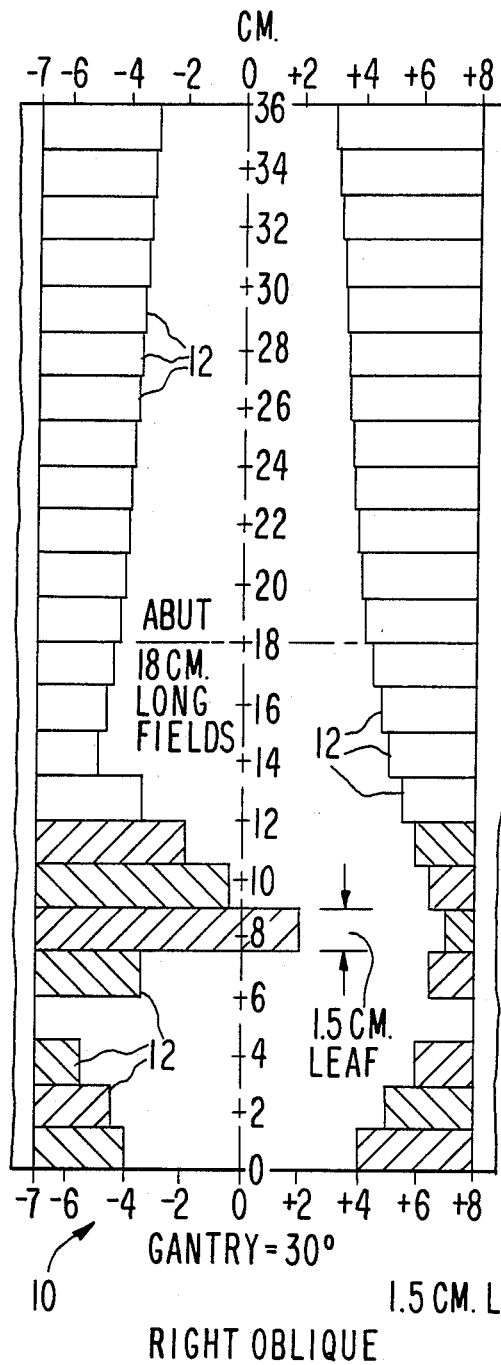
FIG. 1a shows the leaves in the configuration for a right oblique treatment of the region of FIGS. 2-5.

The following is a glossary of terms, elements, and structural members as referenced and employed in the present invention.

10—collimator
11—flat cylinder
12—leaves
14, 16—multileaf half assemblies
18, 20—leaf support frames
22, 23—lower jaws
24—electrical drive motor for half frame
25—threaded shaft
26—rod
27—threaded bushing
28—upper sub-leaves
29—lower sub-leaves
30, 32—rods
34, 36—bushings
38—threaded shaft
40—threaded hole
42—flexible cable
44—motor
46, 48—spur gears
50, 52—subframes
54—correction motor
56—chain
58—sprocket
60—rods
62—upper plate
64—side wall
66—lower plate
68—lip
70—jaw frame
72—bearing

DETAILED DESCRIPTION OF THE PREFERRED EMBODIMENTS

Figure 1B:
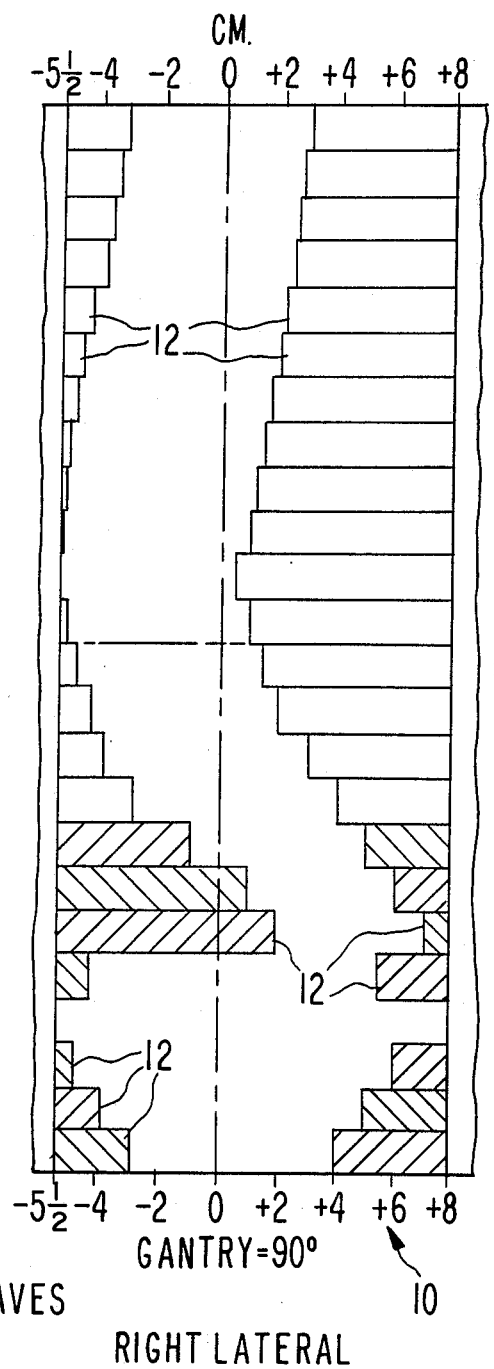
FIG. 1b shows the leaves in the configuration for a right lateral treatment of the region of FIGS. 2-5.

Referring now to the drawings wherein reference numerals are used to designate parts throughout the various figures thereof, there is shown in FIGS. 1a and 1b an example of multi-leaf field shapes of the collimator 10 mounted in a flat cylinder 11 for a complex shaped clinical site, the region of cervix-pelvic nodes-para aortic nodes, as illustrated in FIG. 2. In this example, the field is 36 cm long. Its irregular width is defined by 24 pairs of leaves 12, each producing a 1.5 cm strip shadow in the radiation field at SAD (source-axis distance). The fields are presented for only two gantry angles but they illustrate the range of field shape variation during essentially full gantry rotation.

FIGS. 1a and 1b assuming that both upper and lower conventional jaws are used to define the field rectangular limits (36 cm long, 15 cm wide at 30° gantry angle, 13.5 cm wide at 90° gantry angle) and that the multi-leaf system simply provides the extra shadow blocking required within the rectangle. This permits shallow leaves 12 of 4.5 cm (1.77 inch) thickness tungsten ($18.2 g/cm^3$) for 5% transmission, the usual shielding criterion for shadow blocks, instead of 7 cm or more thickness tungsten for 1% transmission, the usual criterion for jaws. The maximum extension of any leaf into the field in FIGS. 1a and 1b is only 9 cm at SAD and only 2 cm beyond centerline. Assuming a more extreme case of 5 cm extension beyond centerline from a field edge 7 cm from field center; 2 cm beyond center for a 20 cm wide field; and allowing for about 1 cm jaw overlap, the leaves would need to be only 13 cm long projected to SAD, about 6.84 cm (2.7 inches) actual length.

Figure 7:
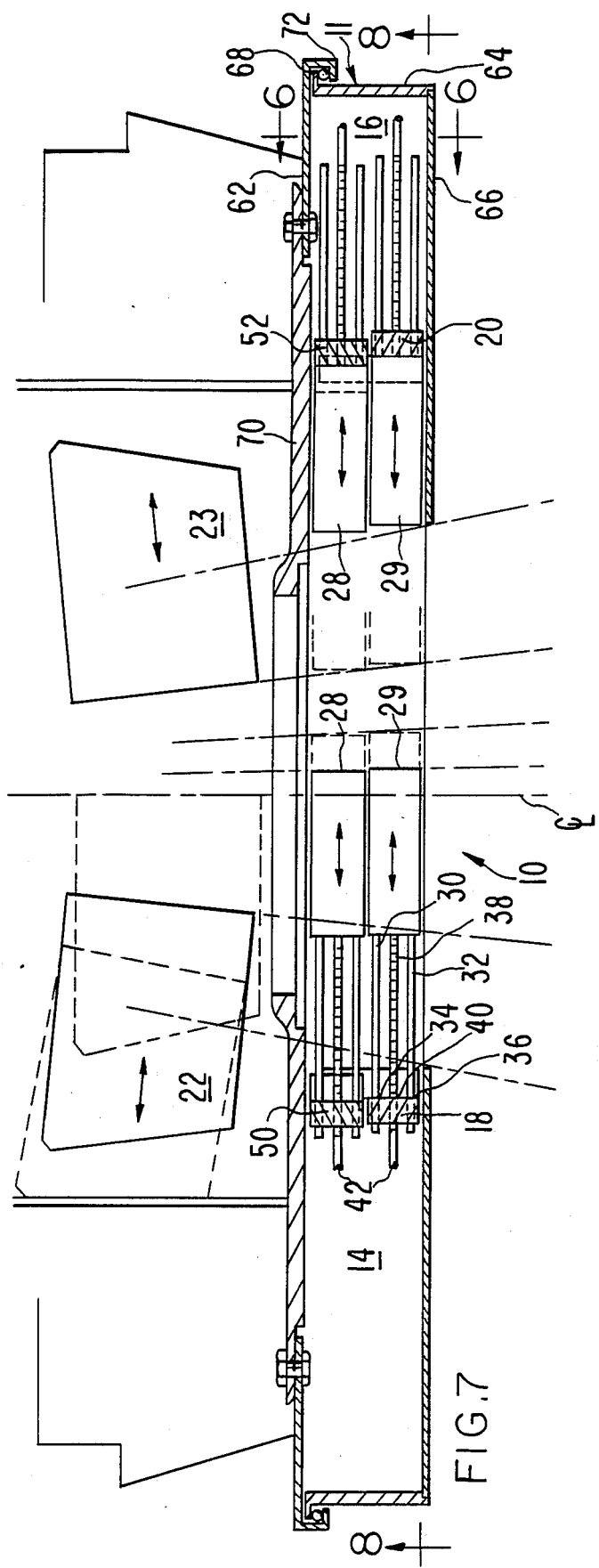
FIG. 7 is a sectional view of the collimator according to the invention as shown in the section plane 7—7 of FIG. 8.
Figure 6:
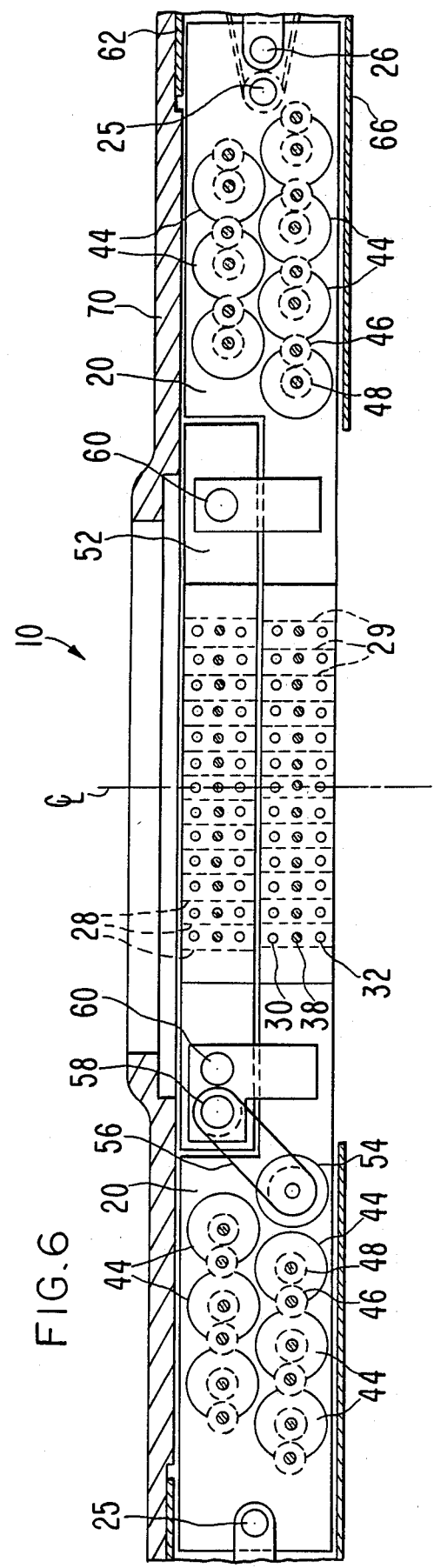
FIG. 6 is a sectional view of the collimator according to the invention as shown in the section plane 6—6 of FIG. 7.
Figure 8:
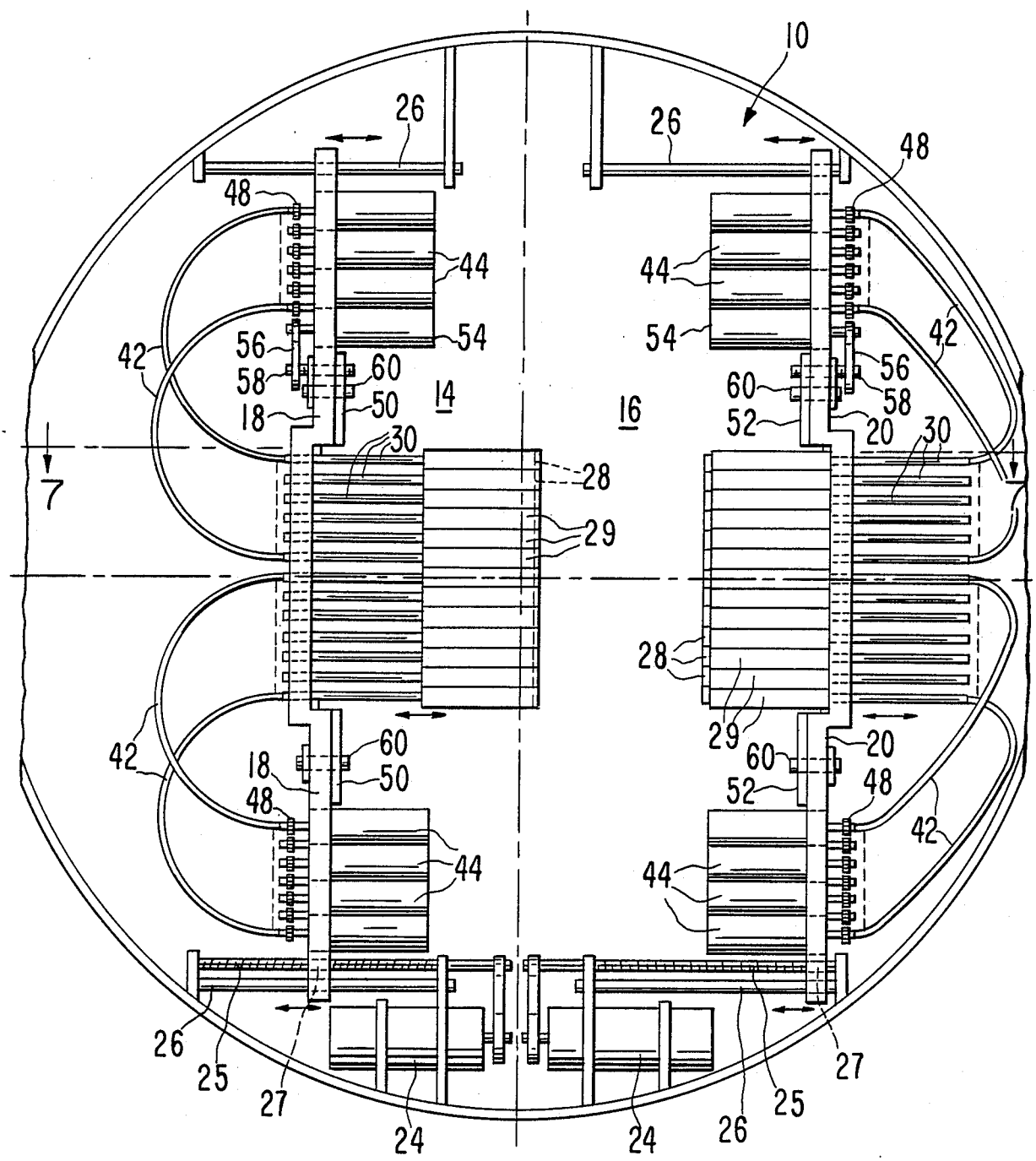
FIG. 8 is a view of the collimator of the invention as seen from the patient treatment region looking toward the x-ray source.

About 95% of all treatment fields fit within a 20 cm×20 cm square. Assuming the projected width of each leaf is 1.5 cm, 13 leaves would cover a 19.5 cm field length. FIGS. 6–8 show such a design. The leaves are mounted in the space presently occupied by the wedge mount of one type of conventional radio-therapy machine, at 52.6 cm from the x-ray source. Each leaf actual dimension is on 0.786 cm (0.31 inch) pitch, is 4.5 cm (1.77 inch) deep, 7.0 cm (2.75 inches) long, and weighs 0.45 kg (0.99 pound) of 18.2 $g/cm^3$ density tungsten. The total of 13 leaf pairs weighs 11.7 kg (25.7 pounds). If a light weight or detachable drive is used, it is conceivable that the multi-leaf assembly could be removed by radiation technologists, one-half (13 pounds, plus drive) at a time. The total weight of all leaves is only 21% the weight of the conventional lower jaws. Each gear motor weighs about ½ pound.

Each multi-leaf half assembly 14, 16 is mounted on a leaf support frame 18, 20 which can be moved in concert with its corresponding lower jaw 22, 23, either by lever connection to the jaw or by chain or other connection to the drive for that jaw or preferably by independent electrical drive 24 for each half frame. Each independent electrical drive 24 is mounted to the cylinder 11 and is coupled by gears, belts or chains to a threaded shaft 25 which drives a leaf support frame sliding on rod 26 and attached to a threaded bushing 27. Thus, the maximum distance any leaf must travel is only the maximum distance it can project into the rectangular field defined by the upper and lower jaws; in this example, 6.6 cm (2.6 inches) actual travel distance relative to the frame.

If the lower jaws 22, 23 are symmetrically driven, one multi-leaf half assembly 14, 16 can be driven as a monoblock to provide dynamic wedge fields up to 12 cm. If the lower jaws are driven independently but are not enlarged in width and travel only up to field center, the multi-leaf half assembly can be driven as a monoblock to travel 12 cm beyond field center, thereby providing dynamic wedge fields up to 24 cm. Thus, independent jaws can be smaller in combination with the "multi-leaf system" than if the independent jaws themselves must be driven past field center and their tails still shield the primary collimator opening.

It is desirable to use straight leaves and to have them travel in a straight line. This minimizes the depth (in SAD direction) of the multi-leaf assembly and simplifies mounting and driving the leaves. It avoids curved tracks and in adapting to existing radiotherapy machines it avoids penetrating into the frame that supports the existing collimator. To achieve approximate alignment of the ends of the leaves with a line from the x-ray target over the full leaf travel, each leaf 12 is actually comprised of two sub-leaves 28, 29, one above the other. Hereinafter upper is taken as meaning closer to the radiation source and lower to mean further from the radiation source. The lower sub-leaf 29 travels slightly faster than the upper sub-leaf 28, so that their ends are staggered to match the angle from the x-ray target. The lower sub-leaf 29 is also slightly wider (2.2 mm in this example) than the upper sub-leaf 28, so that their sides are staggered to match the angle from the x-ray target in the direction at 90° to the leaf travel. The contribution to penumbra due to staggering instead of tapering the leaves is 2.5 mm maximum (80% to 20% dose), at 20 cm field. This will increase total penumbra from a conventional value of 6 mm to $(6^2+2.5^2)0.5=6.5$ mm.

Each sub-leaf is supported by two rods 30, 32 (e.g., $\frac{1}{8}$ inch diameter) which pass through two bushings 34, 36 (e.g., $\frac{1}{4}$ inch outside diameter) in a frame 18, 20, and a threaded shaft 38 (e.g., $\frac{1}{8}$ inch diameter) which passes through a threaded hole 40 in the frame. The individual sub-leaves 28, 29 have sufficient clearance (e.g., 0.2 mm) so that they do not rub on each other, hence avoiding extra friction and the need for radiation resistant dry lubricant (e.g., molybdenum disulphide) in the x-ray beam. Each lower sub-leaf 29 is motor-driven back and forth on micro-processor (not shown) command via the threaded shaft 38, driven through flexible cable 42 from a gear motor 44. The weight of each pair of sub-leaves 28, 29 is about 1 pound, and this weight would need to be supported at 90° gantry angle. It would be desirable to be able to change any leaf position by 5 cm (SAD) in 5° of gantry rotation (0.83 seconds). Adding gear friction, etc., 5 pounds force over 2.7 cm actual travel in 0.8 seconds corresponds to 6.5 inch pounds per second or $10^{-3}$ horsepower, permitting use of a miniature gear motor 44 for each pair of sub-leaves 28, 29, total of 26 such motors for 13 sub-leaf pairs, 13 motors per side. These can be arrayed within the vertical space of the conventional wedge mount. The upper sub-leaf 28 of each split leaf is driven at a slightly lower speed via two spur gears 46, 48 at the gear motor. A rotation counter (not shown) can be installed in the flexible cable drive to each sub-leaf, or to just the upper or lower set of sub-leaves. Each turn of the cable to a $\frac{1}{8}$ inch diameter 12:1 lead screw would correspond to about 0.5 mm change in field edge at SAD. A plus or minus signal for plus or minus one rotation would be sent to a summing circuit and the position of the field edge of each leaf would be displaced digitally and on a CRT. The power to the motor drive would be stopped when this display corresponded to the value of field edge previously set for that leaf at that gantry angle.

The upper sub-leaves 28 are supported on subframes 50, 52 the lower sub-leaves 29 on frames 18, 20. Both subframes 50, 52 are driven from the existing lower jaw drive. Alternatively, motors 54 can be added to drive each frame under control signals independent of the jaw drives. The upper subframes 50 is driven slightly slower than the lower subframe 52 by a correction motor 54, chain 56 and sprocket 58, such that upper subframe slides on rods 60 and such that the frame ends are staggered to match the jaw face slope. The stagger of the sub-leaf ends is then correct for all jaw positions.

FIG. 7 is a drawing showing the planar multi-leaf system in the vertical space normally occupied by the wedge mount. The left side of the collimator 10 shows the lower jaw 22 set for a 20 cm conventional field, with leaves penetrating to 2 cm beyond field axis. The right side of the collimator shows the lower jaw 23 set for a 40 cm conventional field, with the leaves fully withdrawn. This establishes the required diameter of the multi-leaf system housing. The set of 13 split leaves on the right side is driven by a set of 13 gear motors 44, 7 motors being on one side, 6 motors on the other side of the set of leaves. This provides room for the drive cables 42, one for each sub-leaf driven directly by a gear motor 44, the other sub-leaf through a pair of gears 46, 48 at the gear motor. The 13 motors 44 are mounted on the leaf support frame 20 which is driven by a lead screw via a chain from the lower jaw drive system or preferably by a motor 24.

Since the depth of the leaves is so small for 5% transmission in tungsten, it may be clinically acceptable to use single leaves of rectangular cross-section instead of staggered split leaves. The leaf penumbra (20% to 80%) at SAD would be 5 mm maximum (20 cm field), which would increase conventional penumbra from 6 mm to $(6^2+5^2)0.5=7.14$ mm. Avoiding the staggering would reduce the complexity and cost of the mechanical part of the multi-leaf system, but the number of motors and the microprocessor control would remain the same.

The flat cylinder 11 containing the multi-leaf collimator 10 can be mounted rotatably on the radiation head. The flat cylinder 11 includes an upper plate 62, a side wall 64 and a lower plate 66. The side wall 64 has a lip 68. The upper plate 62 is fastened to the jaw frame 70, and extends beyond the side wall and supports a multiplicity of bearings 72 which support the side wall 64 on the lip 68 and permit rotation of the collimator. A single lock may be provided to hold rotational position r the friction of the bearings can be increased to provide holding means. This will permit setting the jaws for a rectangular field at one angle relative to gantry axis (and patient) and the multi-leaf system set at another angle, corresponding more closely to an anatomical edge of interest, such as the spinal cord. This will result in a less stepped edge to the multi-leaf field.

The jaws are tilted as they are opened in order to provide an edge surface parallel to the path of the radiation. In an alternate embodiment, one layer of leaves can be used and the leaves tilted as they are moved in a plane in analogy to the jaws in order to minimize the penumbra. While this alternate embodiment reduces the number of leaves which must be moved it increases the cost, complexity and size of the apparatus.

This invention is not limited to the preferred embodiment and alternatives heretofore described, to which variations and improvements may be made including mechanically and electrically equivalent modifications to component parts, without departing from the scope of protection of the present patent and true spirit of the invention, the characteristics of which are summarized in the following claims.

What is claimed is:

1. An apparatus acting as a collimator in a radiation therapy machine having jaws mounted in a jaw frame for limiting a radiation field to rectangular boundaries, comprising:

leaf means for further limiting and shaping the radiation filed within the rectangular boundaries, said leaf means providing irregular and re-entrant shape radiation fields, said leaf means providing means for shaping fields of greater than 15 cm×15 cm, said leaf means including two sets of leaves, each of said two sets of leaves including a multiplicity of leaves formed of material substantially opaque to x-rays, each said leaf being capable of extension beyond a field mid-line;

mounting means for mounting said leaf means on the jaw frame, said mounting means including a main leaf support frame;

a pair of opposing leaf support subframes, and pair of subframes being coplanar, each said set of leaves being linearly moveably mounted to one of said pair of opposing leaf support substances, said leaf support subframes being linearly moveably mounted within said main leaf support frame; and leaf drive means for providing motion of said leaves relative to said leaf support subframes; and subframe motor drive means for providing motion of said leaf support subframes relative to said main leaf support frame.

2. The apparatus of claim 1 including means for rotatably mounting the apparatus to the jaw frame.

3. The apparatus of claim 1 in which the thickness of the apparatus along the axis of the rectangular x-ray field is less than 10 cm.

4. An apparatus for radiotherapy treatment of a patient comprising:

an electron linear accelerator means for generating x-rays at an x-ray source target;

a set of four moveable jaws mounted on a jaw frame between said x-ray source target and the patient, said set of jaws defining a rectangular x-ray field;

mounting means for mounting a leaf means on said jaw frame, said mounting means including a main leaf support frame;

a pair of subframes, said subframes being substantially coplanar, each of which is linearly movably mounted from said frame;

a multiplicity of leaves of material substantially opaque to x-rays, said leaves being provided with means to make them linearly movable relative to each said subframe;

subframe drive means for independently varying the distance of each subframe from the axis of the rectangular x-ray field, said subframe drive means being substantially coplanar with said subframe;

leaf drive means for independently varying the position of each leaf with respect to its corresponding subframe, said leaf drive means being substantially coplanar with each leaf; and computer control means for controlling said subframe drive means and said leaf drive means to provide a dynamically changing radiation field shape during the course of radiation treatment of the patient.

5. An apparatus acting as a collimator in a radiation therapy machine having jaws mounted in a jaw frame for limiting a radiation field to rectangular boundaries, comprising:

leaf means for further limiting and shaping the radiation field within the rectangular boundaries, said leaf means including two sets of leaves, each of said two sets of leaves including a multiplicity of leaves formed of material substantially opaque to x-rays, each leaf being capable of extension beyond a field mid-line, the length of each said leaf being shorter than half of a maximum field length capability of said jaws measured in the direction and plane of said leaves;

mounting means for mounting said leaf means on the jaw frames, said mounting means including a main leaf support frame;

a pair of opposing leaf support subframes, said pair of subframes being coplanar, each said set of leaves being linearly moveably mounted to one of said pair of opposing leaf support subframes, said leaf support subframes being linearly moveably mounted within said main leaf support frame; and leaf drive means for providing motion of said leaves relative to said leaf support subframes; and subframe motor drive means for providing motion of said leaf support subframes relative to said main leaf support frame.

6. The apparatus of claim 5, including means for rotatably mounting the apparatus to the jaw frame.

7. The apparatus of claim 5 in which the thickness of the apparatus along the axis of the rectangular x-ray field is less than 10 cm.

8. An apparatus for radiotherapy treatment of a patient comprising:

an electron linear accelerator means for generating x-rays at an x-ray source target;

a set of four moveable jaws mounted on a jaw frame between said x-ray source target and the patient, said set of jaws defining a rectangular x-ray field;

mounting means for mounting a leaf means on said jaw frame, said mounting means including a main leaf support frame;

a pair of subframes, each of which is linearly movable mounted from said frame, said subframes being coplanar;

a multiplicity of leaves of material substantially opaque to x-rays, said leaves being provided with means to make them linearly movable relative to each said subframe, each leaf being capable of extension beyond a field mid-line, the length of each said leaf being shorter than half of a maximum field length capability of said jaws measured in the direction and plane of said leaves;

subframe drive means for independently varying the distance of each subframe from the axis of the rectangular x-ray field, said subframe drive means being substantially coplanar with said subframe;

leaf drive means for independently varying the position of each leaf with respect to its corresponding subframe, said leaf drive means being substantially coplanar with each leaf; and computer control means for controlling said subframe drive means and said leaf drive means to provide a dynamically changing radiation field shape during the course of radiation treatment of the patient.

9. The apparatus of claim 8, including means for rotatably mounting the apparatus to the jaw frame.

10. The apparatus of claim 8 in which the thickness of the apparatus along the axis of the rectangular x-ray field is less than 10 cm.

* * * * *